US007977639B2

(12) United States Patent
Maillart et al.

(10) Patent No.: US 7,977,639 B2
(45) Date of Patent: Jul. 12, 2011

(54) DEVICE FOR THE REMOTE OPTICAL DETECTION OF GAS

(75) Inventors: Jean-Luc Maillart, Bouc Bel Air (FR); Nicolas Rouch, Orsay (FR); Emmanuel Soulie, Aix En Provence (FR); Philippe Bernascolle, Tourves (FR)

(73) Assignee: Bertin Technologies, Montigny Le Bretonneux (FR)

( * ) Notice: Subject to any disclaimer, the term of this patent is extended or adjusted under 35 U.S.C. 154(b) by 0 days.

(21) Appl. No.: 12/531,786

(22) PCT Filed: Mar. 19, 2008

(86) PCT No.: PCT/FR2008/000365
§ 371 (c)(1),
(2), (4) Date: Feb. 15, 2010

(87) PCT Pub. No.: WO2008/135654
PCT Pub. Date: Nov. 13, 2008

(65) Prior Publication Data
US 2010/0133435 A1 Jun. 3, 2010

(30) Foreign Application Priority Data

Mar. 22, 2007 (FR) .................................... 07 02091

(51) Int. Cl.
*G01N 21/84* (2006.01)
(52) U.S. Cl. ................................................... 250/338.5
(58) Field of Classification Search ............... 250/338.1, 250/338.5, 339.01, 339.02, 339.13
See application file for complete search history.

(56) References Cited

U.S. PATENT DOCUMENTS

| 3,662,171 | A | | 5/1972 | Brengman et al. |
| 4,773,752 | A | * | 9/1988 | Bechet et al. ................. 356/4.01 |
| 5,306,913 | A | | 4/1994 | Noack et al. |
| 5,594,523 | A | * | 1/1997 | Fujisaki ........................ 396/448 |
| 2002/0195562 | A1 | * | 12/2002 | Salapow et al. ............... 250/330 |
| 2005/0156111 | A1 | | 7/2005 | Racca et al. |
| 2005/0205773 | A1 | * | 9/2005 | Fauci et al. ................. 250/252.1 |
| 2007/0021670 | A1 | * | 1/2007 | Mandelis et al. ............. 600/473 |

FOREIGN PATENT DOCUMENTS

WO   WO 00/42415   7/2000

OTHER PUBLICATIONS

International Search Report and Written Opinion from International Patent Application No. PCT/FR2008/000365, filed Mar. 19, 2008.

* cited by examiner

*Primary Examiner* — David P Porta
*Assistant Examiner* — Marcus H Taningco
(74) *Attorney, Agent, or Firm* — Alston & Bird LLP

(57) ABSTRACT

An remote optical gas detection device comprising a detection housing (30) connected to an electronic power supply unit and to a human-machine interface, this detection housing containing an infrared lens (46) for forming an image on an uncooled microbolometer matrix detector (50), a CCD or CMOS-type camera (64) for observing the observed region under visible light, an assembly of electronic means (68) for controlling the detector and for acquiring and digitizing the infrared signals, as well as a processor (82) for processing these signals in order to detect a gas in the observed region and to determine the concentration thereof.

10 Claims, 2 Drawing Sheets

DEVICE FOR THE REMOTE OPTICAL DETECTION OF GAS

CROSS REFERENCE TO RELATED APPLICATIONS

This application is a national stage application filed under 35 U.S.C. 371 of International Application No. PCT/FR2008/000365, filed Mar. 19, 2008, which claims priority from French Application No. 07/02091, filed Mar. 22, 2007.

FIELD AND BACKGROUND OF THE INVENTION

The invention relates to a remote optical gas detection device, which is applicable, in particular, to the monitoring of industrial sites such as chemical plants, refineries, gas storage facilities, etc.

A device of this type is known from documents EP-A-0 544 962 and WO 03/044499, which includes a thermal camera or an infra-red imaging device associated with a measuring filter and a reference filter which, by turns, are placed on the sighting axis of the camera or the imaging device, the measuring filter having a transmission band which includes at least one specific absorption line of a sought-after gas and being sensitive to the presence of this gas, the reference filter having a transmission band comparable to that of the measuring filter but not including the absorption line or lines of the sought-after gas, and therefore being insensitive to the presence of this gas.

The measuring principle consists in using the background of the observed scene as an infrared source and in highlighting the presence of the sought-after gas on the line of sight and in calculating the concentration thereof by differential processing of the infrared images, spatially in order to process the fluxes derived from different temperature points of the observed region, spectrally so as to distinguish the sought-after gas from the background, and temporally to eliminate false alarms and untimely detections.

This device preferably operates in the IR-III band (from 8 to 14 μm), which is broader than the IR-II band (from 3 to 5 μm), and which enables more flux to be absorbed, atmospheric absorption additionally being weaker in the IR-III band than in the IR-II band.

In this known device, the camera used is a cooled camera which is housed in a suitable housing together with the cooling means thereof, and which is connected to a cabinet containing all of the electrical supply means, camera and filter control means and means for processing the signals obtained, this assembly being heavy, bulky and requiring permanent installation.

SUMMARY OF THE INVENTION

The purpose of this invention, in particular, is to improve this known device, to improve the performance of same and to increase the possibilities for use thereof.

To that end, the invention proposes a remote optical gas detection device, comprising an infrared camera associated with measuring and reference filters mounted successively on the sighting axis of the camera, and means for processing the signals supplied by the camera and corresponding to the fluxes of at least two areas of different temperature of an observed region, characterised in that it includes a detection housing connected to an electrical power supply unit, the detection housing comprising an infrared detector with a matrix of photodetectors, and a filter assembly carried by a rotating disk, this assembly being arranged between the lens and the detector and including power-driven means for successively bringing each filter onto the sighting axis of the lens and detector, the detection housing likewise including electronic boards for controlling the detector, for acquiring and digitizing the infrared signals and for controlling the means for rotating the filter disk, as well as a processor responsible for controlling the operation of the detection housing and for applying gas detection algorithms to the signals supplied by the detector.

In comparison with the above-described known device the device according to the invention has the advantage of being compact, self-contained and easily transportable, of being more easily set up on site and of having a multi-gas detection capability, in particular owing to the integration into the detection housing of the various electronic control and processing boards and the processor for processing the signals supplied by the detector for detecting one or more sought-after gases and the concentration of same on the line of sight.

The filter assembly and the infrared lens are advantageously removable and replaceable by a filter assembly and a lens having different characteristics, which widens the field of use of the device and enables same to be adapted to very specific tasks.

According to other characteristics of the invention:
  the detection housing includes power-driven means for covering and closing the infrared lens with a flap comprising a black body, for protecting the lens during the transport and storage thereof and for periodic re-uniformisation of the infrared image supplied by the detector, for purposes of compensating for thermal drifts and for adapting to the thermal variations of the scene observed;
  the detection housing likewise includes a CCD or CMOS-type matrix array camera, e.g., for observing the targeted region under visible light;
  the detection housing likewise includes means for connecting to a human-machine interface of the screen-keyboard type, and means for connecting to a network including means for connecting to other detection housings of the same type and to a central information processing system;
  inside the detection housing, the infrared detector is attached to a power-driven movable support enabling adjustment of the optical focus;
  the detector includes an un-cooled matrix of microbolometers;
  the detection housing likewise includes means, e.g., such as a 3-axis compass, for locating the orientation of the sighting axis with respect to elevation, relative bearing and azimuth;
  the detection housing is double-walled, at least on the top and sides, and comprises a protective front visor for the infrared lens;
  the detection housing is mounted on a manually oriented platform or on a power-driven turret.

BRIEF DESCRIPTION OF THE DRAWINGS

The invention will be better understood, and other characteristics, details and advantages thereof will become more apparent upon reading the following description, which is given for illustrative purposes with reference to the appended drawings, in which.

MORE DETAILED DESCRIPTION

Figure 1:
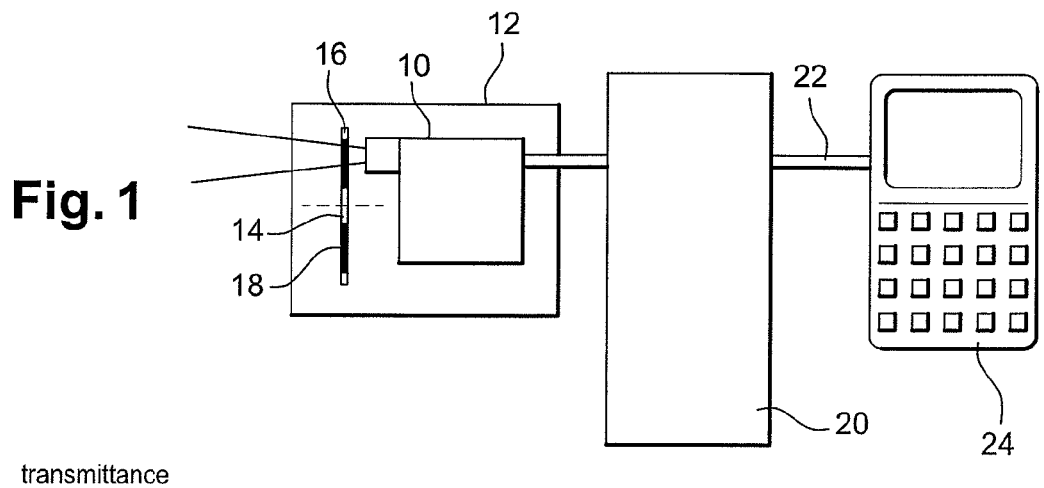
FIG. 1 is a schematic representation of a known remote optical gas detection device.

FIG. 1 is a schematic representation of a known remote optical gas detection device, comprising an infrared camera 10, which is preferably of the cooled type, and which is housed inside a heat-insulating housing 12 likewise comprising a wheel 14 carrying a measuring filter 16 and a reference filter 18, which, by turns, can be brought onto the sighting axis of the camera 10.

The device likewise includes an electrical power supply, control and processing cabinet 20, which is connected to the camera 10 and to the cooling means thereof, as well as to means of rotating the wheel 14 carrying the filters, and which includes means 22 of connecting to an information processing system, e.g., such as a portable computer 24, the cabinet 20 likewise being connectable to a central processing unit.

Figure 2:
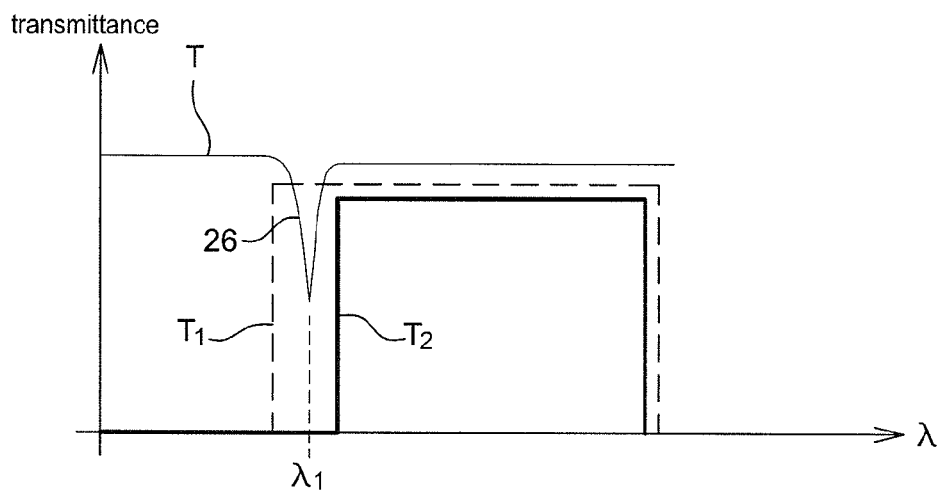
FIG. 2 is a graph illustrating the principle of detecting a gas by means of this device.

The measuring principle is illustrated by the graph of FIG. 2, which shows the variation in the transmittance T of a sought-after gas in relation to the wavelength λ, as well as the transmittance T1 of the measuring filter and the transmittance T2 of the reference filter over a range of wavelengths corresponding to the IR-III band (8 to 14 μm).

The gas transmittance curve T has an absorption line 26 at a wavelength λ1, the amplitude of this absorption line being a function of the concentration of the gas, and the width of same, for example, being of the order of a few tens or hundreds of nm.

The transmittance curve T1 of the measuring filters includes the wavelength λ1 of the absorption line of the detected gas, and extends over a band of wavelengths which is markedly greater than the width of this absorption line.

The transmittance curve T2 of the reference filter is somewhat complementary to the absorption line 26 of the gas, in comparison with the transmittance T1 of the measuring filter, since it extends over substantially the same band of wavelengths as the transmittance T1 of the measuring filter, but does not include the absorption line 26.

When the measuring filter 16 is placed on the optical axis of the camera 10, the flux received by this camera is based on the presence or absence of a cloud of the sought-after gas in the region observed, and on the concentration of this gas on the line of sight of the camera.

When the reference filter 18 is placed on the optical axis of the camera 10, the flux received is independent of the presence or absence of the sought-after gas on the line of sight.

The ratio of the fluxes successively received by the camera 10, through the measuring filter 16, and then through the reference filter 18, provides a quantity which is based on the concentration of the sought-after gas in the region observed, and which is independent of the temperature and transmission of the optical system.

Furthermore, the fluxes supplied by two points or two areas of different temperature of the region observed are successively detected via the two filters, these two points or these two areas being viewed by the camera 10 through the sought-after cloud of gas, which makes it possible to do without the actual emission of the cloud of gas, by differentiating the fluxes coming from these two points or these two areas through the measuring filter, by then differentiating same through the reference filter, and by next establishing the ratio of these differences.

As described, in particular, in the document WO 03/044499, in order to detect several gases, it is likewise possible to use a filter assembly the transmission bands of which are determined relative to one another on the basis of the absorption lines of the gases to be detected, so that a filter which is usable as a reference filter for detecting a gas is usable as a measuring filter for detecting another gas, or vice versa, the filters being combined in pairs or groups, each pair or group being intended for detecting one or more gases.

It is also possible to use a filter assembly having transmission bands which are spread over a band of observation wavelengths and which possibly overlap, in order to obtain an image of the region observed in each transmission band, the resulting images next being called upon to reconstitute images viewed through the broadband measuring filters and images viewed through the broadband reference filters.

Figure 3:
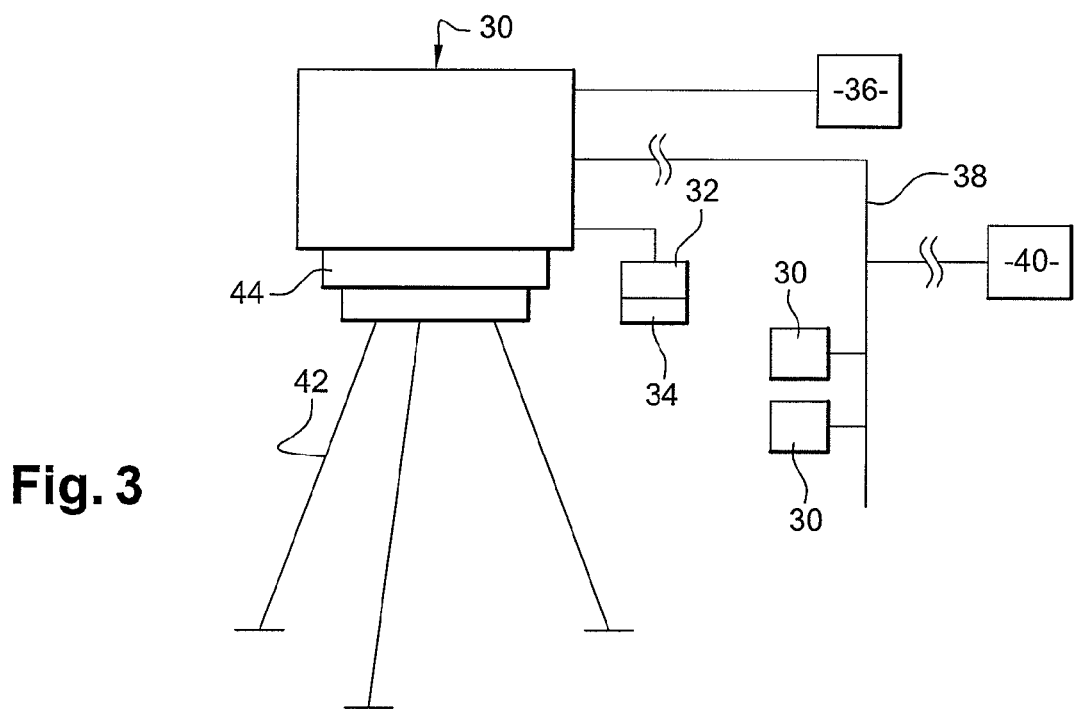
FIG. 3 is a schematic representation of a detection device according to the invention.

The remote optical gas detection device according to the invention differs substantially from this known device in that, as shown schematically in FIG. 3, the detection housing 30 includes not only a preferably uncooled microbolometer matrix infrared detector (which enables continuous monitoring over long periods of time), an infrared lens and a power-driven filter assembly, but likewise a set of electronic boards for controlling the infrared detector and for acquiring and digitizing the infrared signals supplied by this detector, and boards for controlling the various mechanisms contained inside this housing, as well as means of locating the orientation of the sighting axis, a colour CCD or CMOS camera for observing the observed region under visible light, an operation processor for controlling all of the means used and for applying gas detection algorithms to the signals obtained, and electronic circuits utility systems ensuring the distribution and protection of the internal power supply circuits of the housing 30, from the general electrical power supply provided by an external housing 32 connected to a battery 34 or an electrical distribution network.

The detection housing 30 is connected to a human-machine interface 36 and to a network 38 comprising means of connecting to other detection housings 30 of the same type and to a remote central information processing unit 40. The detection housing 30 can be mounted on a manually-oriented platform held by a tripod 42 or on a power-driven turret 44 controlled and powered from the detection housing 30.

In one particular embodiment of the invention, the detection housing 30 has dimensions of the order of 670 mm×280 mm×330 mm and a weight of approximately 18 kg, and the power supply unit 32 equipped with the battery 34 has dimensions of the order of 170 mm×120 mm×125 mm and a weight of approximately 4 kg, with the result being that the entire device according to the invention is transportable, easily set up on site and self-contained.

Figure 4:
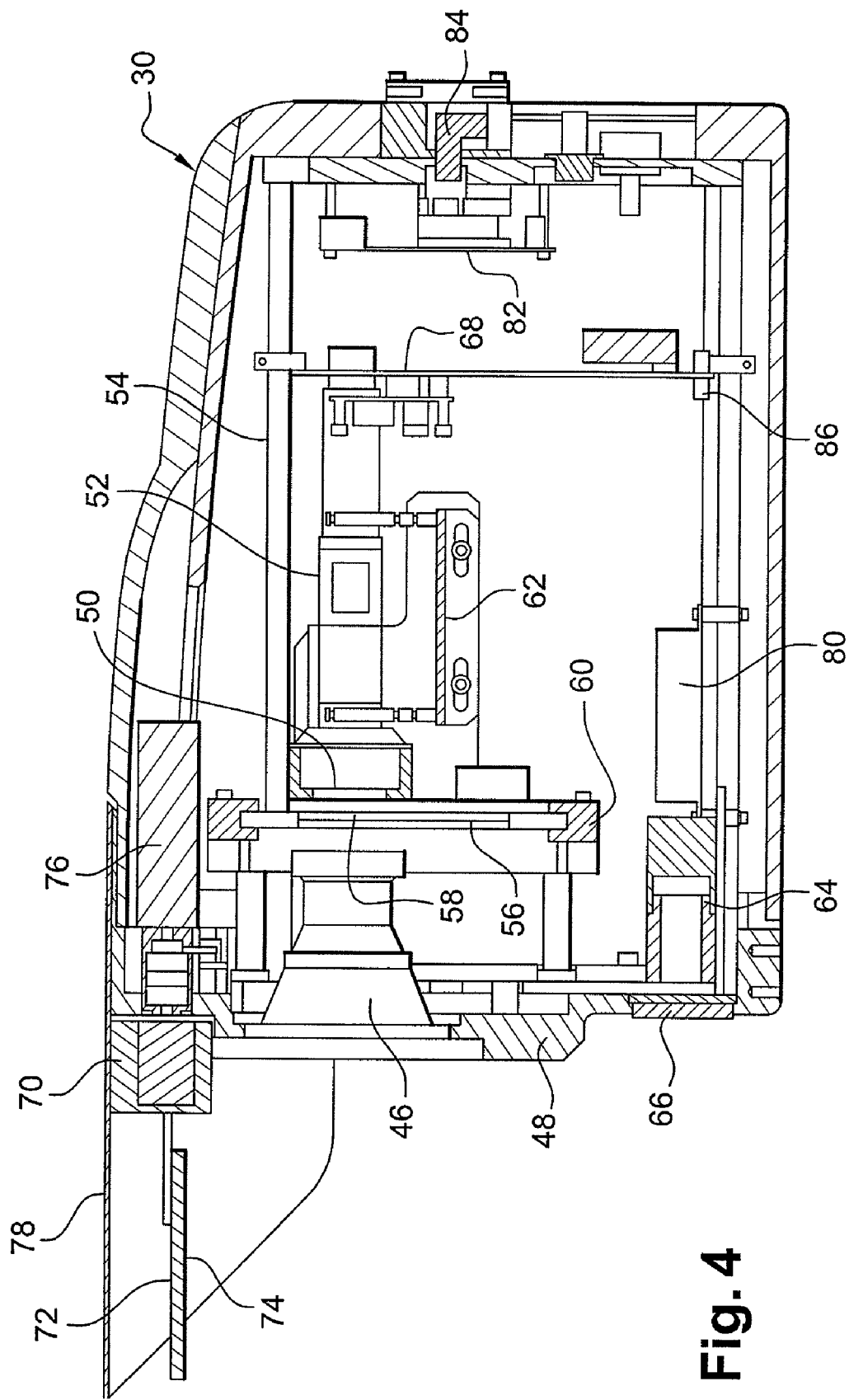
FIG. 4 is an axial section view of the detection housing of this device.

In a more detailed manner, as shown in FIG. 4, the detection housing 30 includes an infrared lens 46, which is attached by the front end thereof behind a window of the front wall 48 of the housing 30, and an uncooled microbolometer matrix infrared detector 50, which is mounted behind the lens 46 on a power-driven support 52, which is guided inside the housing 30 on a frame 54 which holds the detection housing components, the axial movement of the detector 50 support 52 enabling optical focussing based on the operating conditions (lens characteristics 46, operating temperature, configuration of the filter assembly, etc.). This arrangement has the advantage of preserving the scale and exact field of the camera shot in the event of a modification in the focussing due to a thermal drift, and of therefore compensating for this drift without any spatial modification of the scene observed, in terms of field and analysis resolution.

A disk 56 carrying filters 58 is placed between the rear end of the lens 46 and the detector 50 and is mounted removably in a support 60 which comprises power-driven means for rotating the disk 56 and indexing means for locating the angular position of the disk about the axis of rotation thereof and of the filter placed on the axis of the lens 46, the number of filters 58 being carried by the disk 56 being 6, for example.

Electronic boards for controlling the detector 50 and for acquiring and digitizing the infrared signals received by the detector are mounted at 62 inside the housing, behind the detector 50.

A CCD or CMOS camera 64 is mounted inside the housing 30 beneath the infrared lens 46, behind a window 66 of the front wall of the housing, in order to take images of the observed scene under visible light.

Electronic command-control means 68 responsible for controlling the various mechanisms of the housing 30 are held by the frame 54, behind the detector 50 and the support thereof 52, these mechanisms comprising the power-driven disk 56 carrying the filters 58, the power-driven support 52 for the detector 50, temperature control means, as well as means 70 of covering and protecting the lens 46, which are held by the upper portion of the front face 48 of the housing and which can pivot between an operating position of the detector 50, shown in FIG. 4, and a turned-down position on the front end of the lens 46, these means 70 comprise a flap 72 carrying a black body 74 on the face thereof which is intended to cover the front end of the lens 46, and driving means 76 mounted on the inside of the housing 30 and enabling the flap 72 to be pivoted about a transverse axis between the two aforesaid positions of same.

The flap 72 enables the front end of the lens 46 to be covered and closed off, in order to protect same during periods of non-use of the detector 50, in particular during the transport and storage of the housing 30, the black body 74 placed on the front end of the lens 46 enabling periodic re-uniformisation of the infrared image for adapting to thermal variations of the region observed and for compensating for the thermal drifts of all of the components of the entire image acquisition chain, including the lens 46 and the window behind which it is placed.

Mechanism 70 is mounted at the front of the housing 30, beneath a visor 78 attached to the upper wall of the housing 30 and extending forward, for protecting the lens 46 against illumination via direct solar radiation.

An additional protection against overheating resulting from exposure to the sun is provided by a double wall of the housing 30, on the lateral faces and upper face thereof, as shown in FIG. 4.

Means 80 are mounted inside the housing, e.g., beneath the power-driven support 52 for the detector 50, for locating the orientation of the sighting axis, with respect to relative bearing, elevation and azimuth, these means comprising a 3-axis compass, for example.

Inside the housing, the rear face of the housing 30 holds a processor 82 responsible for controlling all of the components of the detection housing, and for applying the gas detection algorithms to the signals supplied by the detector 50, the processor also being responsible for communications with external means (human-machine interface 36, network 38, central processing unit 40) and for controlling the power-driven turret 44 onto which the housing 30 can be fastened. The processor 82 is situated in a rear compartment of the housing 30, which is separated from the infrared detector 50 situated at the front of the housing and which is also in contact with cooling means 84 comprising radiators and fans enabling the heat to be discharged via the rear face of the housing 30.

Finally, electronic means 86 mounted on the frame 54, at the rear of the housing, are connected to the power supply unit 32 in order to ensure the distribution of electrical energy and the protection of the internal power supply means of the housing 30.

The device according to the invention operates as follows:
at start-up, the six filters carried by the disk 56 are used by turns in order to detect all of the gases which are detectable by means of the combinations of the six filters, the rotation cycle of the disk then being continuous and each of the six spectral paths corresponding to the six disks of the filter being used for signal acquisition.

Alternatively, an operator can select certain gases from amongst those which are detectable by means of the combinations of the six filters of the disk 56, and to limit the signal acquisitions to the filters corresponding to the selected gases. Based on the number of required spectral paths, this enables the analysis cycle to be accelerated. This selection can be carried out either locally, by means of the human-machine interface 36, or remotely, from the central processing unit 40 via the network 38.

The detection is active throughout the entire image formed by the lens 46 on the detector 50. The first analysis of the imagined scene requires approximately 30 to 40 seconds in order to arrive at optimal detection performance. Next, the measurements taken and the display can be refreshed at a frequency of the order of 2 seconds.

The operator can likewise select particular regions in the image formed on the detector 50, which will be processed as regions of interest or as forbidden regions, according to circumstances.

Generally speaking, the invention makes it possible to ensure continuous monitoring of an observed site over long periods of time, and without acting on the controls, to be free of the effect of variations in temperature of the scene observed on determining the concentrations of the gases detected, to reduce false alarms, and to improve the response time of the device and the spectral selectivity thereof.

The invention claimed is:

1. A transportable and self-contained remote optical gas detection device for continuous monitoring of an observed site, the device comprising a detection housing connected to an electrical power supply unit, the detection housing comprising an infrared detector with a matrix of photodetectors, an infrared lens mounted in front of the detector, a filter assembly held by a rotating disk, this assembly being arranged between the infrared lens and the detector and including power-driven means for successively bringing each filter onto the sighting axis of the infrared lens and detector, the detector being attached to a power-driven support guided in movement inside the detection housing for adjusting the optical focus based on operating conditions for compensating a thermal drift without any spatial modification of a scene observed, in terms of field and analysis resolution, the detection housing further including electronic boards for controlling the detector, for acquiring and digitizing the infrared signals and for controlling the means of rotating the disk carrying the filters, and a processor responsible for controlling the operation of the detection housing and for applying gas detection algorithms to the signals supplied by the detector.

2. A device according to claim 1, characterised in that the detection housing includes power-driven means for covering and closing the infrared lens with a flap comprising a black body, for protecting the lens during the transport and storage thereof and for periodic re-uniformisation of the infrared image supplied by the detector, for purposes of compensating for thermal drifts and for adapting to the thermal variations of the site observed.

3. A device as claimed in claim 1, characterised in that detection housing further includes a CCD or CMOS-type matrix array camera for observing the targeted site under visible light.

4. A device as claimed in claim 1, characterised in that the detection housing further includes means for connecting to a human-machine interface of the screen-keyboard type.

5. A device as claimed in claim 1, characterised in that the detection housing includes means for connecting to a network including means of connecting to other detection housings of the same type and to a central information processing system.

6. A device as claimed in claim 1, characterised in that the detector further includes an uncooled matrix of microbolometers.

7. A device as claimed in claim 1, characterised in that the infrared lens and the filter assembly are removable.

8. A device as claimed in claim 1, characterised in that the detection housing includes means for locating the orientation of the sighting axis with respect to elevation, relative bearing and azimuth.

9. A device as claimed in claim 1, characterised in that the detection housing is double-walled, at least on the top and sides thereof, and includes a protective front visor for the infrared lens.

10. A device as claimed in claim 1, characterised in that the detection housing is mounted on a manually oriented platform or on a power-driven turret.

* * * * *